US011730556B2

(12) United States Patent
Penny et al.

(10) Patent No.: US 11,730,556 B2
(45) Date of Patent: Aug. 22, 2023

(54) COMPACT ACTUATION CONFIGURATION AND EXPANDABLE INSTRUMENT RECEIVER FOR ROBOTICALLY CONTROLLED SURGICAL INSTRUMENTS

(71) Applicant: Asensus Surgical US, Inc., Durham, NC (US)

(72) Inventors: Matthew Robert Penny, Holly Springs, NC (US); Kevin Andrew Hufford, Cary, NC (US); Paul Wilhelm Schnur, Pipersville, PA (US)

(73) Assignee: Asensus Surgical US, Inc., Durham, NC (US)

( * ) Notice: Subject to any disclaimer, the term of this patent is extended or adjusted under 35 U.S.C. 154(b) by 258 days.

(21) Appl. No.: 16/932,654

(22) Filed: Jul. 17, 2020

(65) Prior Publication Data
US 2021/0169595 A1    Jun. 10, 2021

Related U.S. Application Data

(63) Continuation-in-part of application No. 16/732,307, filed on Dec. 31, 2019.
(Continued)

(51) Int. Cl.
| *A61B 34/00* | (2016.01) |
| *A61B 34/30* | (2016.01) |
| *B25J 9/12* | (2006.01) |
| *B25J 15/00* | (2006.01) |
| *A61B 46/00* | (2016.01) |
| *A61B 90/98* | (2016.01) |

(52) U.S. Cl.
CPC .............. *A61B 46/30* (2016.02); *A61B 34/30* (2016.02); *A61B 34/70* (2016.02); *A61B 90/98* (2016.02); *B25J 9/126* (2013.01); *B25J 15/0028* (2013.01)

(58) Field of Classification Search
CPC ..... A61B 34/30; A61B 1/00149; A61B 34/70; A61B 34/71; A61B 46/10; A61B 2017/00367; A61B 2017/00477; A61B 34/37; B25J 15/0028; B25J 15/0033
See application file for complete search history.

(56) References Cited

U.S. PATENT DOCUMENTS 6,436,107 B1 *  8/2002  Wang ................... A61B 34/75
                                                                606/139
9,107,685 B2 *  8/2015  Parihar ............ A61B 17/2804
(Continued)

OTHER PUBLICATIONS

PCT, International Search Report and Written Opinion of the International Searching Authority for International Application No. PCT/US2020/42671 (dated Oct. 28, 2020).

*Primary Examiner* — Julian W Woo

(57) ABSTRACT

A robotic system assembly comprises a robotic manipulator including an actuator assembly and a surgical instrument having a base body mountable to the actuator assembly. The base includes a first control input and a second control input, wherein the first and second control inputs are positioned on different sides of the base. The actuator assembly is moveable between open and closed positions to facilitate removal and replacement of surgical instruments. When in the closed positions, drive elements of the actuator assembly are positioned to drive the first and second control inputs of the surgical instrument to cause end effector movement or actuation.

20 Claims, 16 Drawing Sheets

Related U.S. Application Data

(60) Provisional application No. 62/874,988, filed on Jul. 17, 2019, provisional application No. 62/787,254, filed on Dec. 31, 2018, provisional application No. 62/875,003, filed on Jul. 17, 2019, provisional application No. 62/874,985, filed on Jul. 17, 2019, provisional application No. 62/874,982, filed on Jul. 17, 2019.

(56) References Cited

U.S. PATENT DOCUMENTS

| | | |
|---|---|---|
| 11,432,890 B2 * | 9/2022 | Traina .................... A61B 90/57 |
| 2010/0191251 A1 | 7/2010 | Scott et al. |
| 2010/0292707 A1 | 11/2010 | Ortmaier et al. |
| 2013/0144116 A1 | 6/2013 | Cooper et al. |
| 2017/0071628 A1 | 3/2017 | Cooper et al. |
| 2017/0071692 A1 | 3/2017 | Taylor et al. |

\* cited by examiner

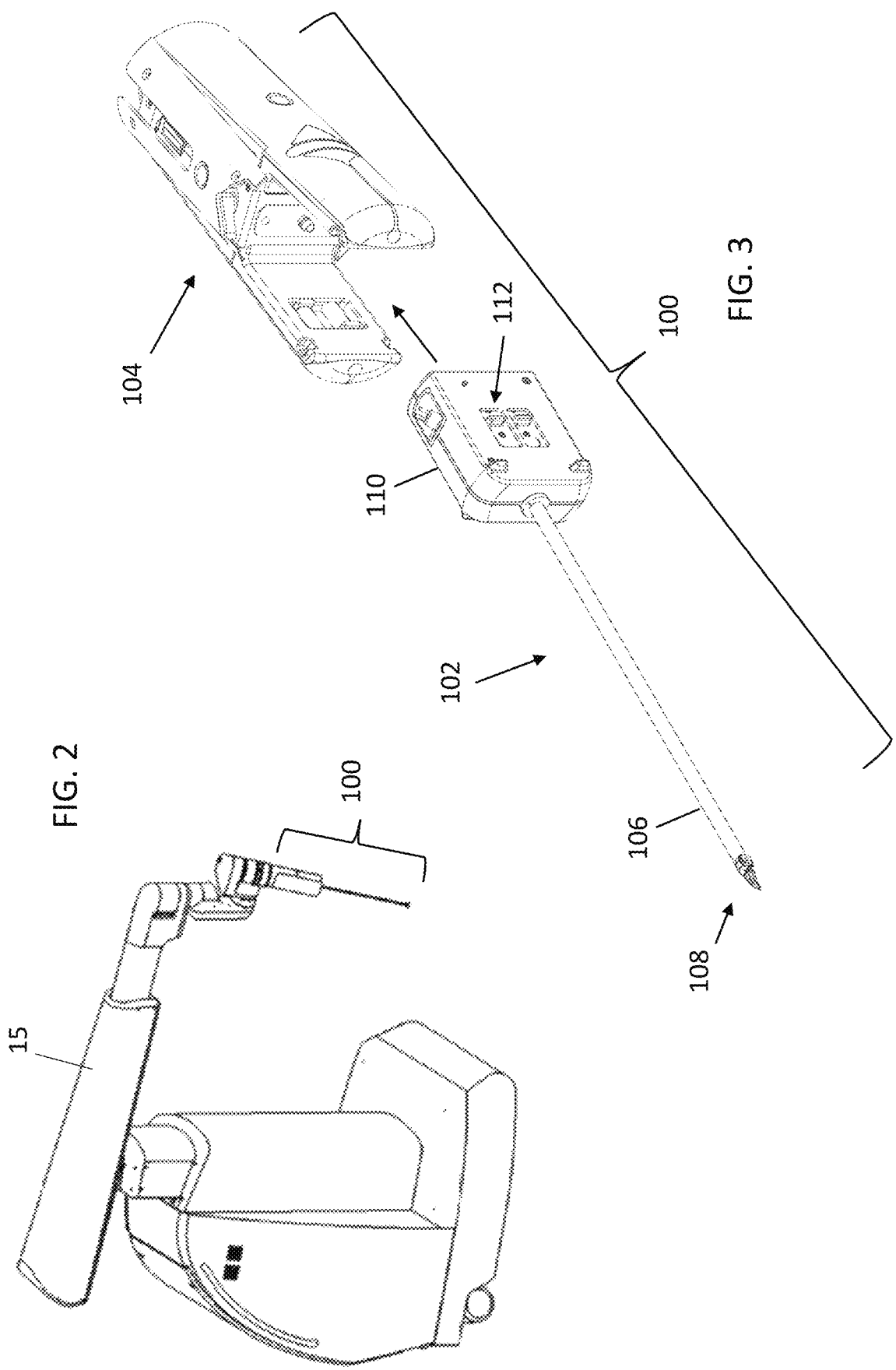

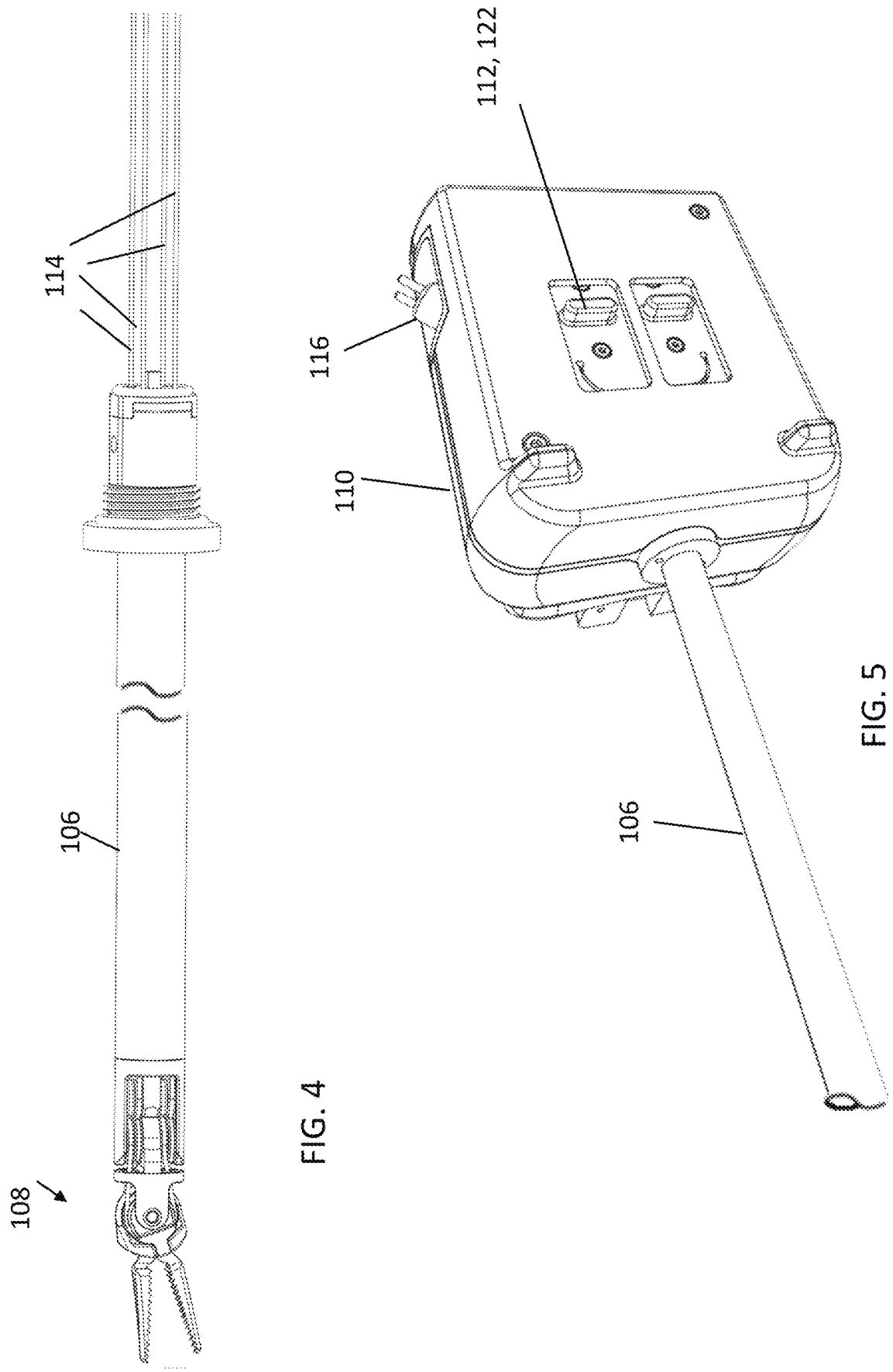

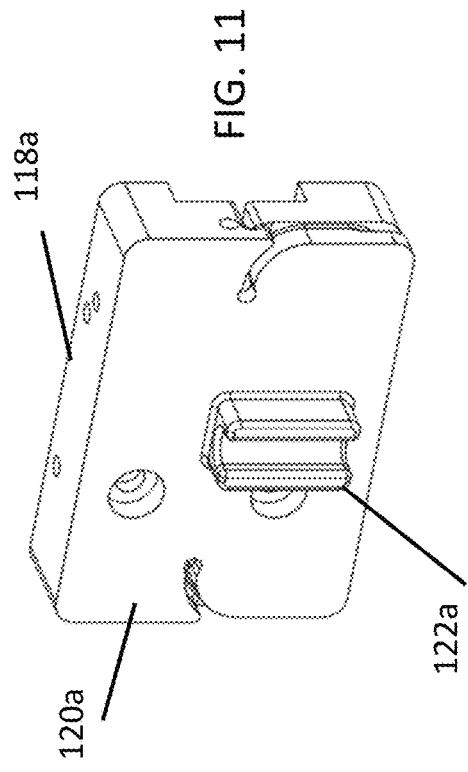
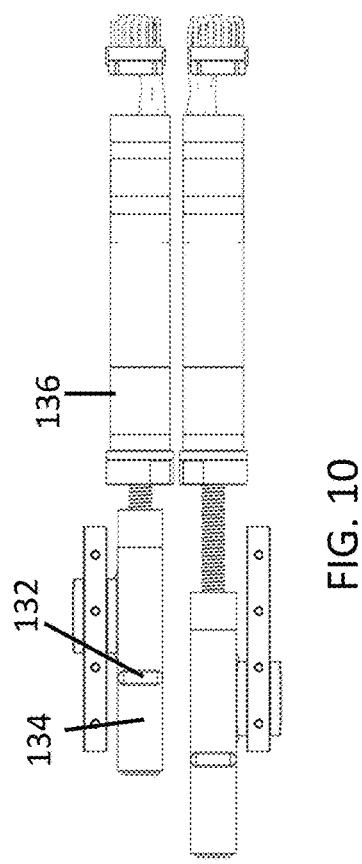
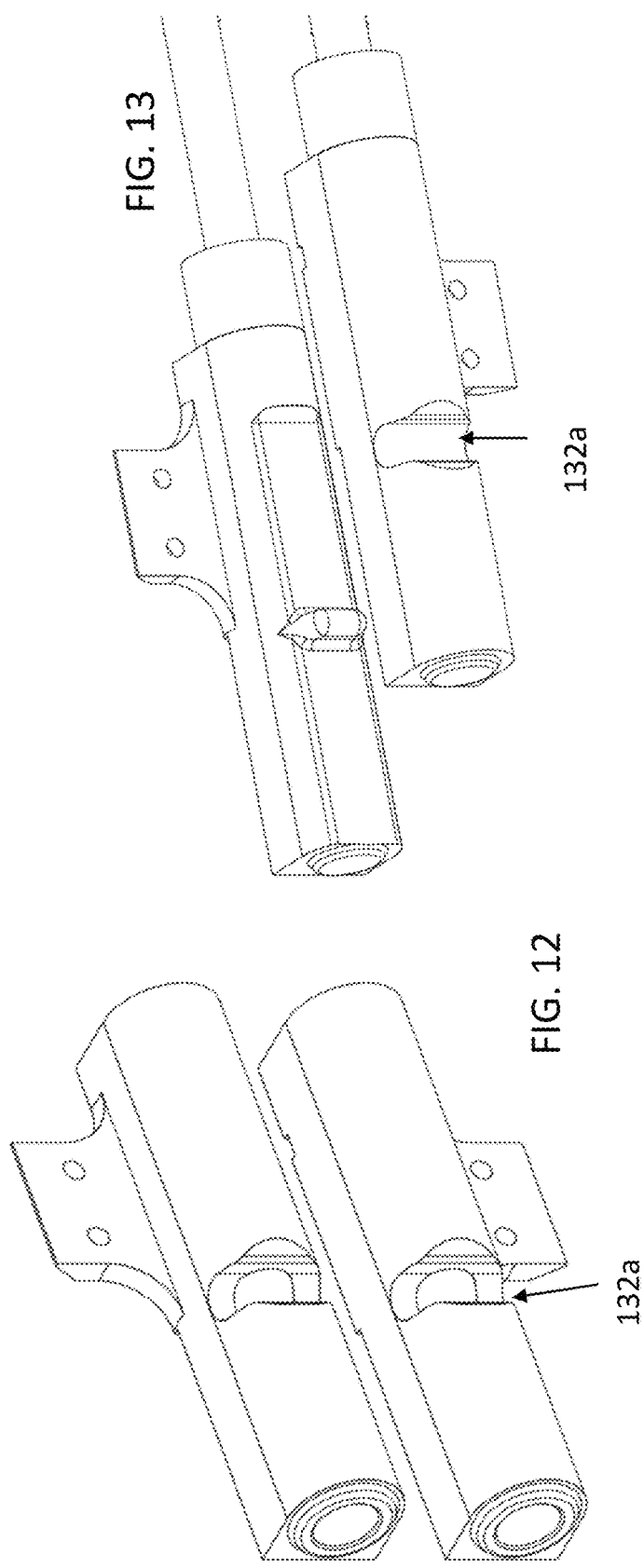

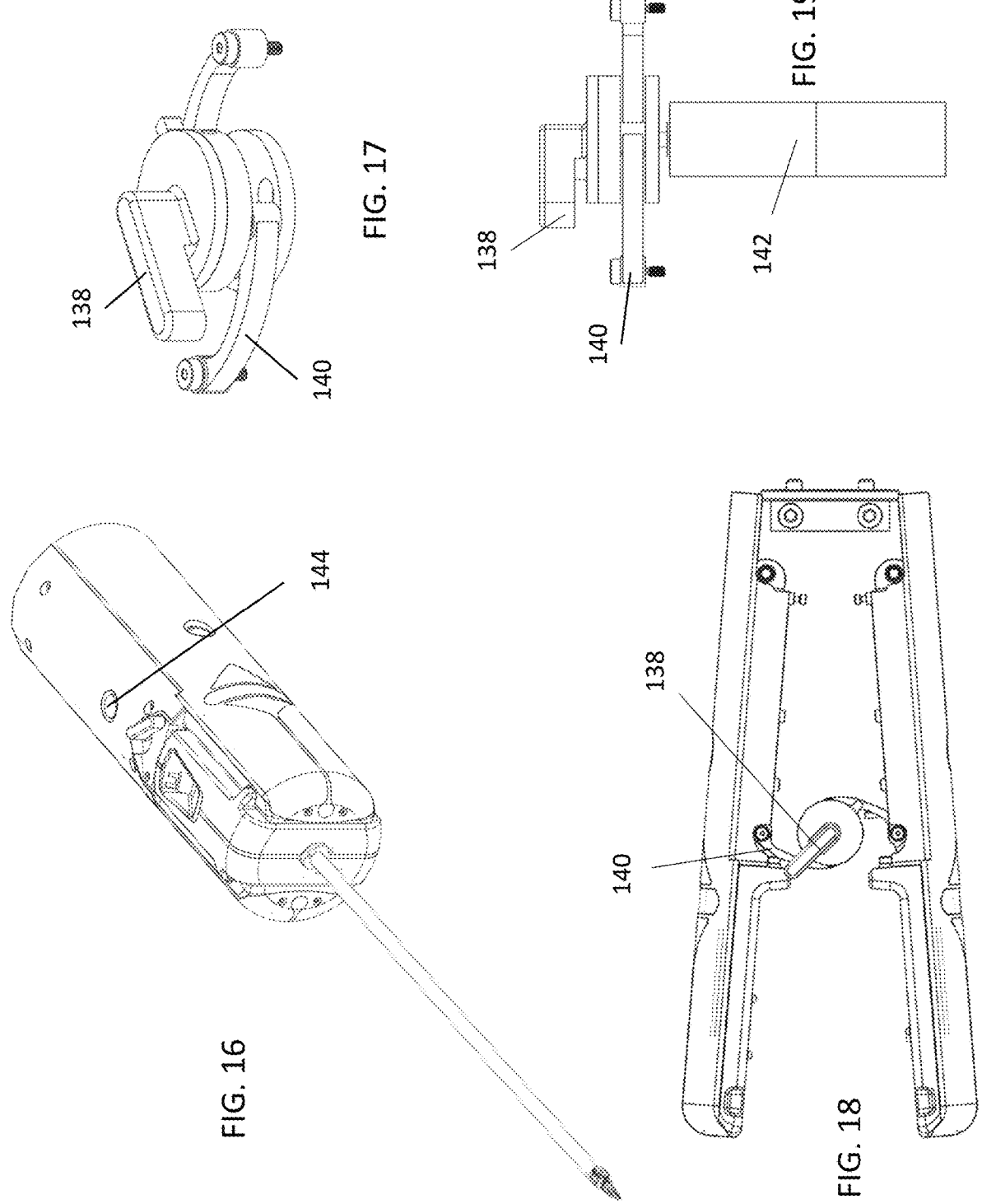

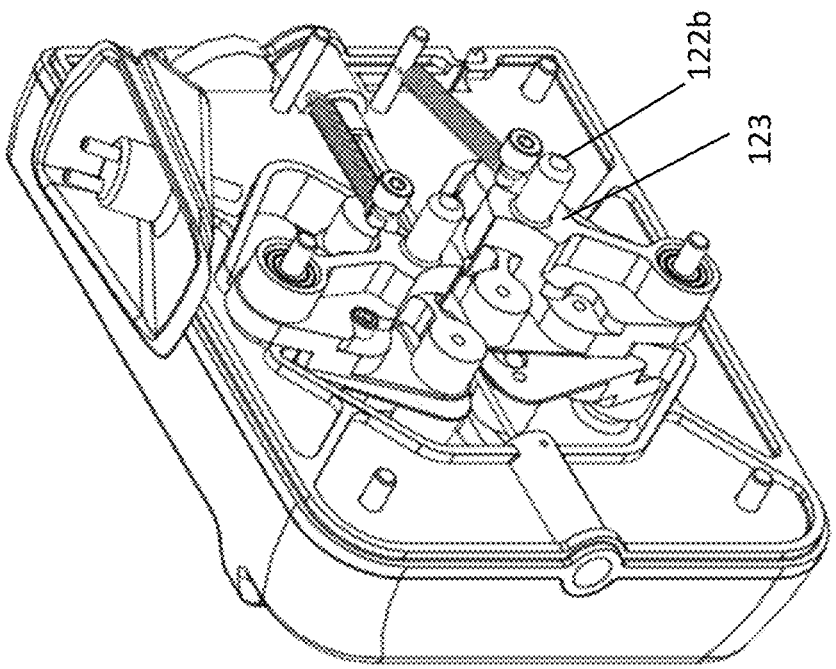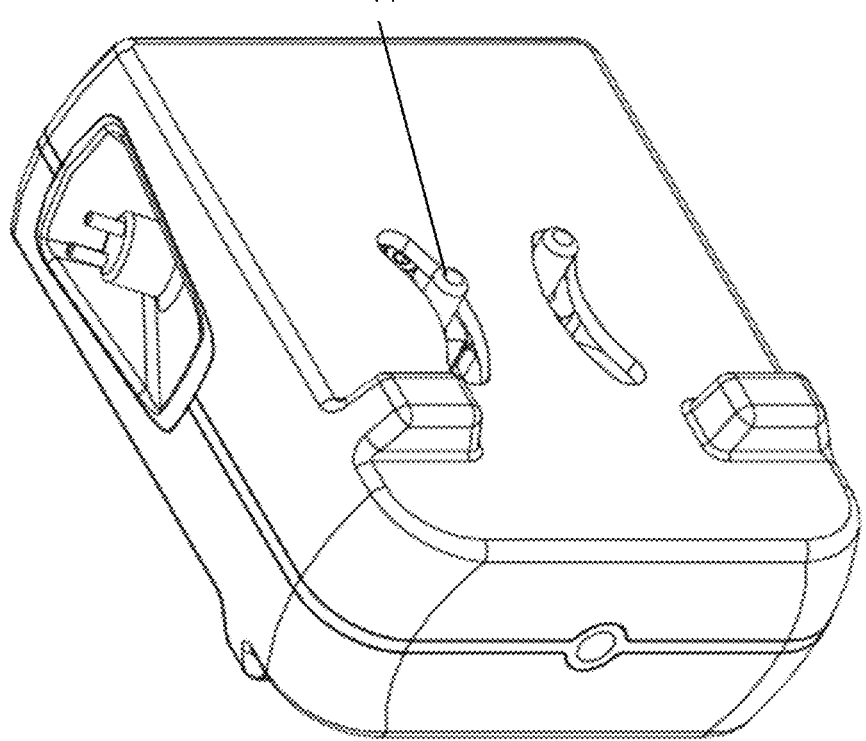

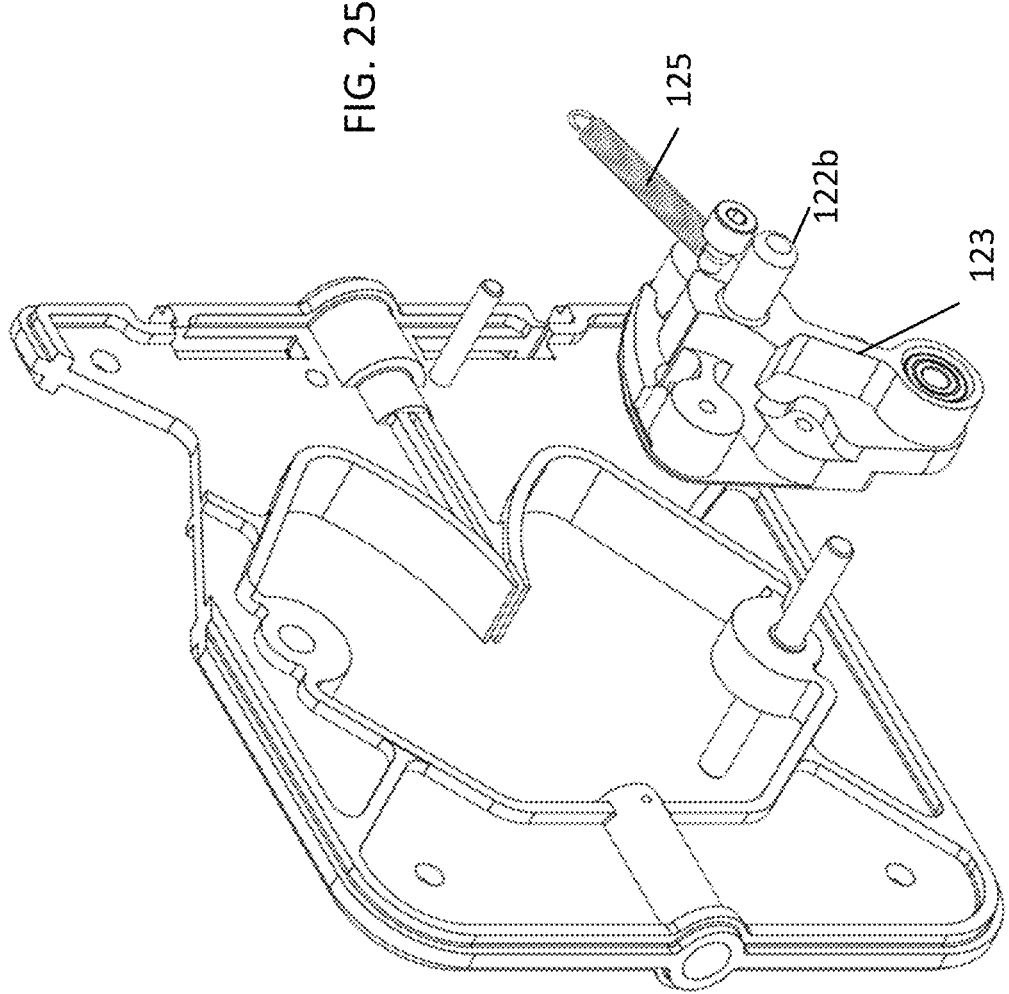

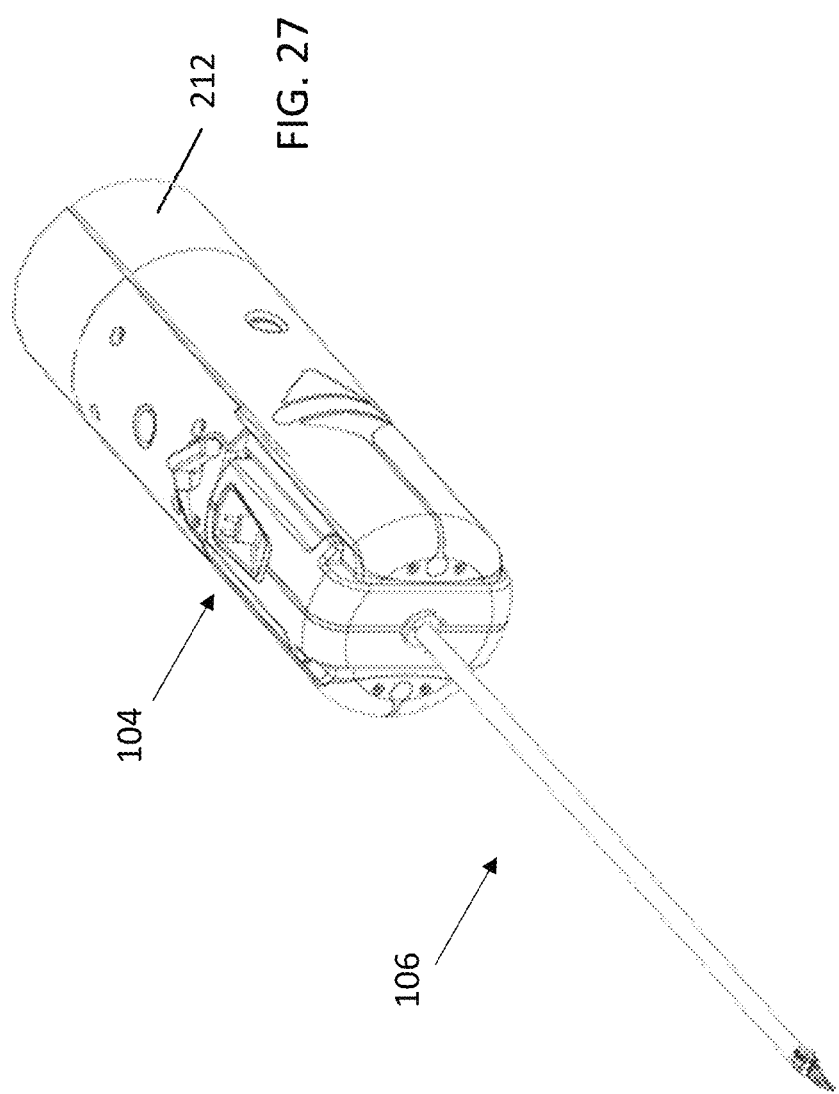

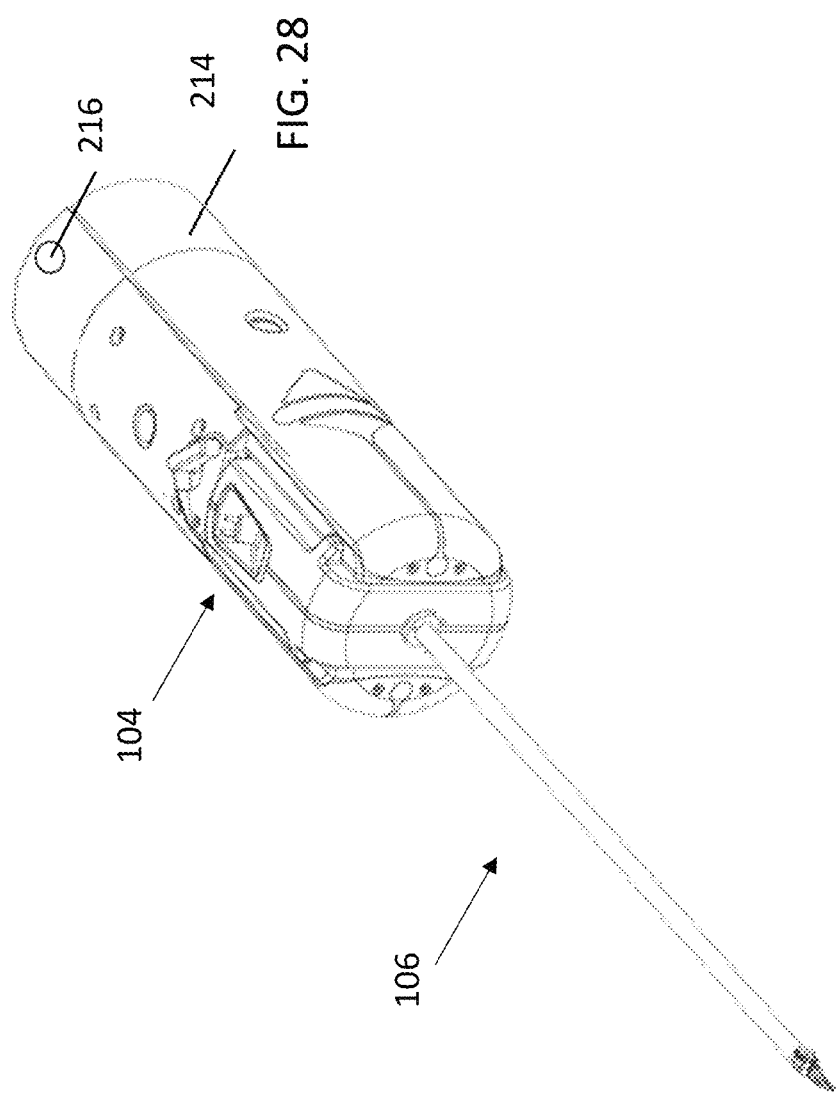

COMPACT ACTUATION CONFIGURATION AND EXPANDABLE INSTRUMENT RECEIVER FOR ROBOTICALLY CONTROLLED SURGICAL INSTRUMENTS

This application is a continuation in part of U.S. application Ser. No. 16/732,307, filed Dec. 31, 2019, which claims the benefit of the following U.S. Provisional applications: U.S. 62/874,988, filed Jul. 17, 2019 and U.S. 62/787,254, filed Dec. 31, 2018. This application further claims the benefit of U.S. Provisional Application Nos.: U.S. 62/874,988, filed Jul. 17, 2019, U.S. 62/875,003, filed Jul. 17, 2019, U.S. 62/874,985, filed Jul. 17, 2019, and U.S. 62/874,982, filed Jul. 17, 2019.

TECHNICAL FIELD OF THE INVENTION

The present invention relates to the field of surgical devices and systems, including those using electromechanical actuation.

BACKGROUND

There are various types of surgical robotic systems on the market or under development. Some surgical robotic systems use a plurality of robotic arms. Each arm carries a surgical instrument, or the camera used to capture images from within the body for display on a monitor. Typical configurations allow two or three instruments and the camera to be supported and manipulated by the system. Input to the system is generated based on input from a surgeon positioned at a master console, typically using input devices such as input handles. Motion and actuation of the surgical instruments and the camera is controlled based on the user input. The image captured by the camera is shown on a display at the surgeon console. The console may be located patient-side, within the sterile field, or outside of the sterile field.

The robotic arms/manipulators include a portion, typically at the terminal end of the arm, that is designed to support and operate a surgical device assembly. The surgical device assembly includes a surgical instrument having a shaft and a distal end effector on the shaft. The end effector is positionable within a patient.

Typically, a proximal housing on the instrument shaft includes actuation mechanisms that receive motion transferred from actuators that drive functions of the instrument. The end effector may be one of many different types of that are used in surgery including, without limitation, end effectors having one or more of the following features: jaws that open and close, section at the distal end of the shaft that bends or articulates in one or more degrees of freedom, a tip that rolls axially relative to the shaft, a shaft that rolls axially relative to the manipulator arm. The instrument actuators for driving the motion of the end effector, which might be motors or other types of motors (e.g. hydraulic/pneumatic), are often positioned in the terminal portion of the robotic manipulator. In some cases, they are positioned in the proximal housing of the surgical device assembly, and for other configurations some are in the proximal housing while others are in the robotic manipulator. In the latter example, some motion of the end effector might be driven using one or more motors in the terminal portion of the manipulator while other motion might be driven using motors in the proximal housing.

The instruments are exchangeable during the course of the procedure, allowing one instrument to be removed from a manipulator and replaced with another. Engaging the proximal housing with the actuator interface at the manipulator may involve the use of mechanical snaps, magnetic engagement, or sliding interfaces that rigidly dock the instrument to the manipulator in order to resist external forces from both the robot and the patient. There is a mechanical interface to engage with surgical instruments. At this interface, motion generated using the instrument actuators within the robotic manipulator is communicated to one or more mechanical inputs of the proximal housing to control the degrees of freedom of the instrument and, if applicable, its jaw open-close function. This motion may be communicated through a drape positioned between the sterile instrument and the non-sterile manipulator arm. In some current robotic systems, the mechanical control interface includes actuators disposed only on one side or plane of an instrument. For example, in the configuration shown in U.S. Pat. No. 6,491,701, all of the driven elements 118 that receive mechanical motion are on the same face of the housing 108 at the proximal end of the instrument shaft 102.

In the embodiment shown in U.S. Pat. No. 9,358,682, a transverse slider pin 314 extends laterally from one side of the case mounted to the proximal end of the instrument. It is moveable to open and close jaws of the instrument (FIG. 18 of the patent). When the instrument is mounted to the manipulator arm, the slider pin 314 is received by a corresponding component 430 (FIG. 19) in the manipulator arm. When it is necessary to open/close the jaws, the component 430 is translated on a carriage by motors in the laparoscopic instrument actuator 400 of the manipulator arm, thereby advancing the slider pin 314 to actuate the jaws. US Application 2016/20160058513 also shows a robotically controlled surgical instrument that is removably attached to a manipulator arm and describes a similar configuration in which a slider pin is used for jaw actuation. It further describes a system that can provide not only jaw actuation but additional electromechanically-driven movements of the instrument end effector, such as articulation or rotation. However, the motors for those additional movements are enclosed in the housing at the proximal end of the instrument and thus do not require transfer of mechanical motion from motors in the arm to mechanical actuators of the housing.

This application describes a robotically controlled surgical instrument having a plurality of mechanical actuators at its proximal end. These mechanical actuators are arranged to receive motion transferred from electromechanical actuators within the manipulator arm in order to drive various end effector functions or motion, such as jaw actuation, pitch, roll, and/or yaw. The actuators are arranged in a configuration that is compact and that allows the manipulator arm to engage with instruments or adapters of varying sizes. The described embodiments also enable configuration of instruments or adapters such that the actuating interfaces may exist on more than one surface of the instrument or adapter, including surfaces that face away from one another.

BRIEF DESCRIPTION OF THE DRAWINGS

FIG. 2 is a perspective view of a robotic manipulator arm with the receiver and instrument assembly mounted to it;

FIG. 3 are a perspective view showing the receiver of FIG. 2 and the surgical instrument separated from the receiver;

FIG. 4 shows the surgical instrument with the base removed;

FIG. 5 shows the proximal part of the surgical instrument;

FIG. 10 is a side elevation view of the carriage and motor assemblies of one arm of the receiver;

FIG. 11 is an alternate embodiment of a carriage for the instrument base;

FIGS. 12 and 13 are perspective views of alternate embodiments of carriages for one of the arms of the receiver;

FIG. 16 is a perspective view showing the instrument mounted to the receiver;

FIG. 17 is a perspective view showing the lever and linkages of the receiver;

FIG. 18 is similar to FIG. 15, but shows a portion of the receiver housing removed to allow the expansion mechanism to be seen;

FIG. 19 is a side elevation view of the instrument and lever of FIG. 17 and the associated motor;

FIG. 23 is a perspective view of an alternative embodiment of the base;

FIG. 24 is similar to FIG. 23, but shows a portion of the housing removed;

FIG. 25 is a perspective view showing one of pulley mechanisms and springs of the embodiment of FIG. 23.

FIG. 27 is similar to FIG. 16 and further shows a graphical user interface disposed on the manipulator end effector.

FIG. 28 is similar to FIG. 27, but illustrates features for provided force feedback to a user during manual repositioning of the manipulator.

DETAILED DESCRIPTION

Figure 1:
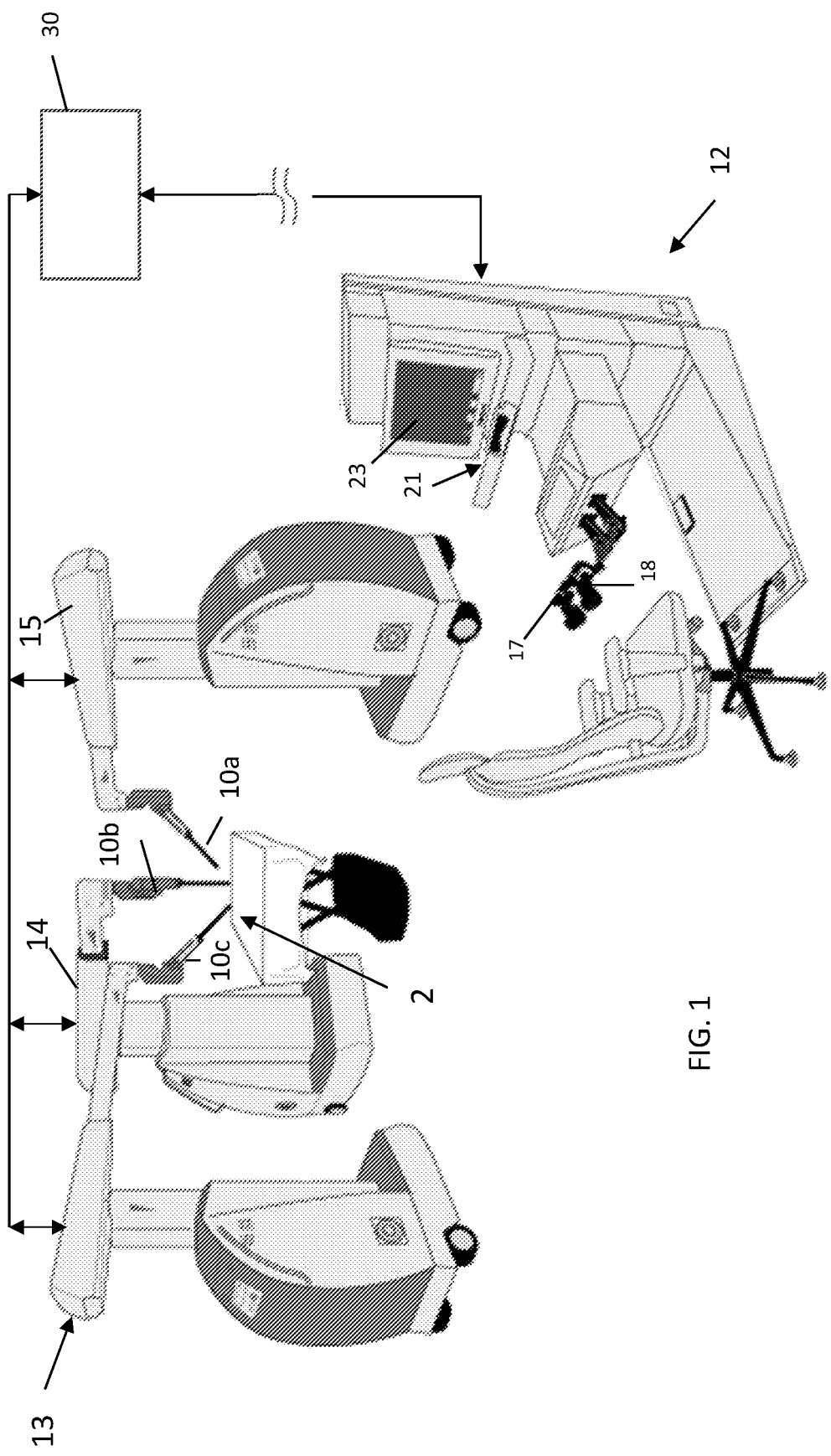
FIG. 1 is a perspective view of a robot-assisted surgical system on which the configurations described herein may included.

Although the concepts described herein may be used on a variety of robotic surgical systems, the embodiments will be described with reference to a system of the type shown in FIG. 1. In the illustrated system, a surgeon console 12 has two input devices such as handles 17, 18. The input devices 12 are configured to be manipulated by a user to generate signals that are used to command motion of a robotically controlled device in multiple degrees of freedom. In use, the user selectively assigns the two handles 17, 18 to two of the robotic manipulators 13, 14, 15, allowing surgeon control of two of the surgical instruments 10a, 10b, and 10c disposed at the working site (in a patient on patient bed 2) at any given time. To control a third one of the instruments disposed at the working site, one of the two handles 17, 18 may be operatively disengaged from one of the initial two instruments and then operatively paired with the third instrument, or another form of input may control the third instrument as described in the next paragraph. A fourth robotic manipulator, not shown in FIG. 1, may be optionally provided to support and maneuver an additional instrument.

One of the instruments 10a, 10b, 10c is a camera that captures images of the operative field in the body cavity. The camera may be moved by its corresponding robotic manipulator using input from a variety of types of input devices, including, without limitation, one of the handles 17, 18, additional controls on the console, a foot pedal, an eye tracker 21, voice controller, etc. The console may also include a display or monitor 23 configured to display the images captured by the camera, and for optionally displaying system information, patient information, etc.

A control unit 30 is operationally connected to the robotic arms and to the user interface. The control unit receives user input from the input devices corresponding to the desired movement of the surgical instruments, and the robotic arms are caused to manipulate the surgical instruments accordingly.

The input devices 17, 18 are configured to be manipulated by a user to generate signals that are processed by the system to generate instructions used to command motion of the manipulators in order to move the instruments in multiple degrees of freedom and to, as appropriate, control operation of electromechanical actuators/motors that drive motion and/or actuation of the instrument end effectors.

Sensors may optionally be used to determine the forces that are being applied to the patient by the robotic surgical tools during use. For example, a force/torque sensor on the surgical robotic manipulator may be used to determine the haptic information needed to provide force feedback to the surgeon at the console. U.S. Pat. No. 9,855,662, entitled Force Estimation for a Minimally Invasive Robotic Surgery System, describes a surgical robotic system in which sensors are used to determine the forces that are being applied to the patient by the robotic surgical tools during use. It describes the use of a 6DOF force/torque sensor attached to a surgical robotic manipulator as a method for determining the haptic information needed to provide force feedback to the surgeon at the user interface. In the presently disclosed embodiments, a sensor of this type may be optionally be positioned on or just proximal to the receiver 104. The surgical system allows the operating room staff to remove and replace the surgical instruments 10a, b, c carried by the robotic manipulator, based on the surgical need. When an instrument exchange is necessary, surgical personnel remove an instrument from a manipulator arm and replace it with another.

In general, the assembly includes a surgical instrument having a base configured such that its driven members (which receive mechanical drive input to actuate functions of the instrument's end effector) are disposed on more than one side, face, facet or plane of a base at the proximal end of the instrument. The base is one that in use is received by an arm within which is electromechanical or hydraulic actuators that drive mechanical outputs. To maintain sterility of the surgical instrument, the system is designed to facilitate use of a surgical drape positioned between the base of the instrument and the corresponding mechanical drive outputs on the arm. Positioning the instrument actuators on more than one side, facet, face or plane of the instrument aids in spreading out the forces and deflections imparted by these actuators on the drape, allowing transfer of multiple mechanical inputs to the instrument while preserving the drape.

Referring to FIGS. 2 and 3, this application describes an assembly 100 of a surgical instrument 102 and a receiver 104. The receiver 104 is configured to removably receive the instrument 102. The receiver may be mounted to a support or manipulator 15, which may be a robotic manipulator that robotically manipulates the instrument 102 in one or more degrees of freedom during a procedure, or a support that remains stationary during the course of surgery embodiments of a surgical instrument for a robotic surgical system. When the surgical instrument 102 and receiver 104 are assembled, the receiver transfers motion generated by electromechanical actuators (e.g. motors or hydraulic/pneumatic actuators) in the receiver 104 or the arm 15 to mechanical actuators of the instrument to cause motion of a part of the instrument. Examples of types of motion include, without limitation, articulation in one or more degrees of freedom (pitch, yaw), bending in one or more degrees of freedom, end effector roll, jaw actuation, etc. As discussed above, the surgeon moves the input devices 17, 18 (FIG. 1) to provide inputs into the system, and the system processes that information to develop commands for the relevant electromechanical actuators in order to move the instruments and, as appropriate, operate the instrument end effectors.

The surgical instrument 102 includes an elongate shaft 106, which is preferably rigid but which may be flexible or partially flexible in alternative systems. An end effector 108 is positioned at the distal end of the shaft 106, and a proximal body or base assembly 110 is at the proximal end. The base assembly 110 (which will also be referred to as the "base") may include an enclosed or partially enclosed structure such as a housing or box, or it may be a frame or plate. The base 110 includes mechanical input actuators 112 exposed to the exterior of the surgical instrument 102. In FIG. 3, two actuators 112 are exposed at a first lateral face of the base 110. A second two actuators 112 are exposed at the second, opposite, lateral face of the base 110, preferably but optionally in a configuration identical or similar to the configuration shown in FIG. 3. See the rear view of the base 110 shown in FIG. 22.

Each of the actuators 112 is moveable relative to the base 110 between first and second positions. In the specific configuration shown in the drawings, the actuators are longitudinally moveable relative to the housing between a first (more distal) position and a second (more proximal) position such as that shown in FIG. 3. The direction of motion, however, is not required to be longitudinal and can extend in any direction.

In this configuration, the base assembly thus has four drive inputs 122 exposed to its exterior. In this configuration the base has two parallel planar faces, with two of these inputs positioned on each of the faces. While it may be preferred to include the inputs on opposite sides of the proximal body, other arrangements of inputs on multiple faces of the proximal body can instead be used. Each of these configurations advantageously arranges the drive inputs in a way that maximizes the distance between control inputs, minimizing stresses in the sterile drape that, as discussed below, is positioned between the proximal body and the receiver 104.

Referring to FIG. 4, drive cables 114 extend through the shaft 106 to the end effector 108. Many different types of instruments having any of a variety of functions may be used in the disclosed system. The instrument depicted in the drawings is the type described in commonly-owned co-pending application Ser. No. 16/732,306, entitled Articulating Surgical Instrument, filed Dec. 31, 2019, which is incorporated herein by reference. It makes use of four drive cables 114 two of which terminate at one of the jaw members and the other two of which terminate at the other jaw member. This can be two cables looped at the end effector (so each of the two free ends of each cable loop is at the proximal end) or it can be four individual cables. As described in the co-pending application, the tension on the cables is varied in different combinations to effect pitch and yaw motion of the jaw members and jaw open-close functions. Other instruments useful with the system will have other numbers of cables, with the specific number dictated by the instrument functions, the degrees of freedom of the instrument and the specific configuration of the actuation components of the instrument. Note that in this description the terms "tendon," "wire," and "cable" are used broadly to encompass any type of tendon that can be used for the described purpose.

Figure 7:
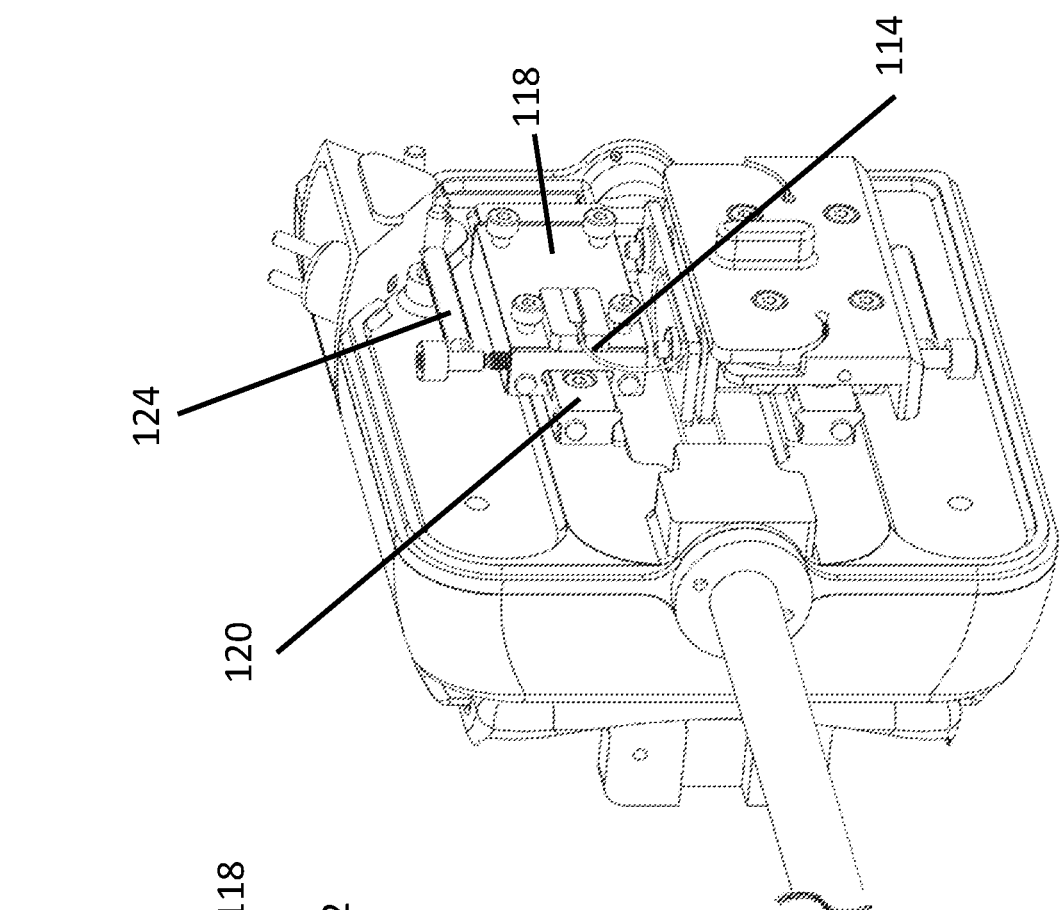
FIG. 7 is similar to FIG. 6, but shows a portion of the upper carriage removed.
Figure 6:
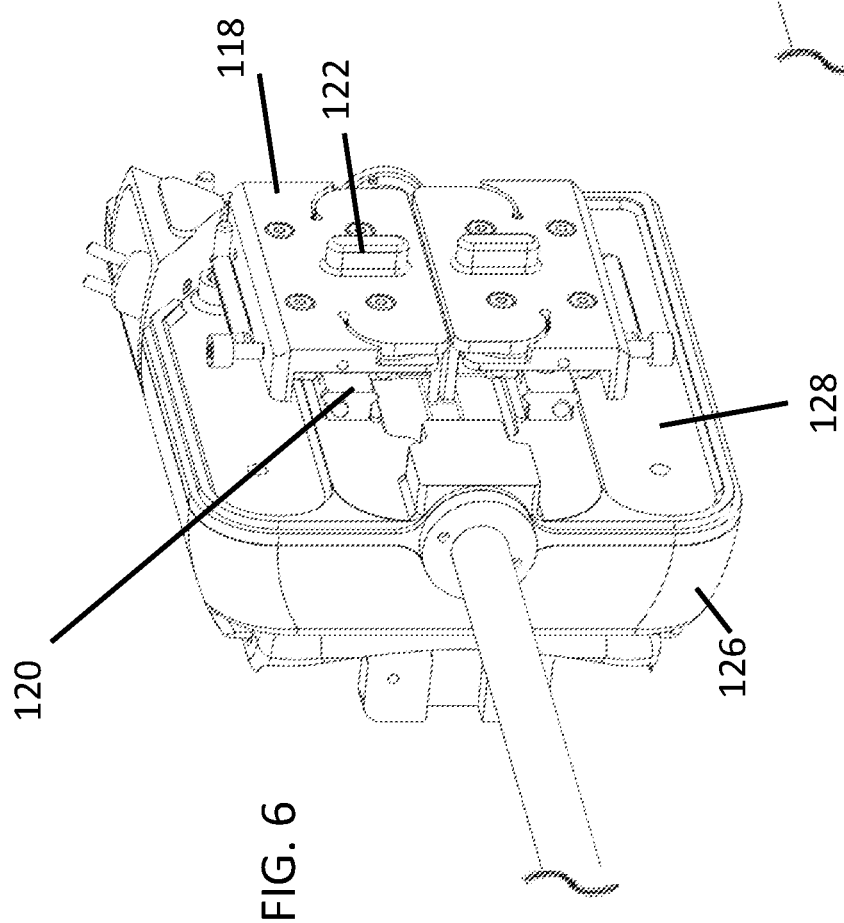
FIG. 6 is similar to FIG. 5, but shows a portion of the housing removed.

The four cables extend to the base 110 assembly. In this embodiment, where the base includes a housing, the cables extend from the shaft 106 into the housing where they are engaged to the actuators 112. FIG. 6 shows the base with a portion of the housing removed to allow a clearer view of the actuators 112. Each actuator 112 includes a carriage 118 moveable along a rail 120. In this embodiment these structures are oriented for longitudinal movement of the carriage, but in others motion can be in a different direction. A portion of the carriage 118 is exposed through a window in the base, and includes a drive input or member 122 that extends laterally from the carriage and that may optionally extend through the outermost plane of the window (see FIG. 5). In FIG. 7 the carriage for the upper actuator is partially disassembled, showing that the proximal end of a cable 114 is mounted to the carriage 118. The cable may extend around a pulley or through a cable path defined by features of the base assembly. In this configuration, a second cable end is similarly connected to the carriage 118 of the lower actuator in FIG. 7, and the remaining two cable ends are connected to the carriages at the opposite face (not shown) of the base 100. In this way, the base assembly is arranged to have actuators 112 exposed at at least two sides or faces of the base. Each actuator 112 is connected to one of the cables 114 so that movement of the actuator in a first direction relative to the base increases tension on the corresponding cable, and movement of the actuator in a second, different (or opposite) direction decreases tension on that cable. In the illustrated embodiment, movement of an actuators carriage 118 in a proximal direction increases or decreases (depending on the routing of the cable) tension on that cable, and movement of the carriage in a distal direction has the opposite effect on the cable tension.

In this embodiment, an extension spring 124 is connected between the carriage 118 and a supporting structure of the base (in this case to the outer housing 126 or a partition 128 that divides the interior of the housing into two laterally adjacent regions). Application of force to the carriage to actively move the carriage in the direction against the spring force (in this case the distal direction) increases the tension on the corresponding cable. When the applied force is released, the spring force moves the carriage back to or towards a home position and reduces the tension on the cable. In other embodiments, the carriage may instead be actively moved in both directions in lieu of the use of spring force for one direction of motion.

Figure 8:
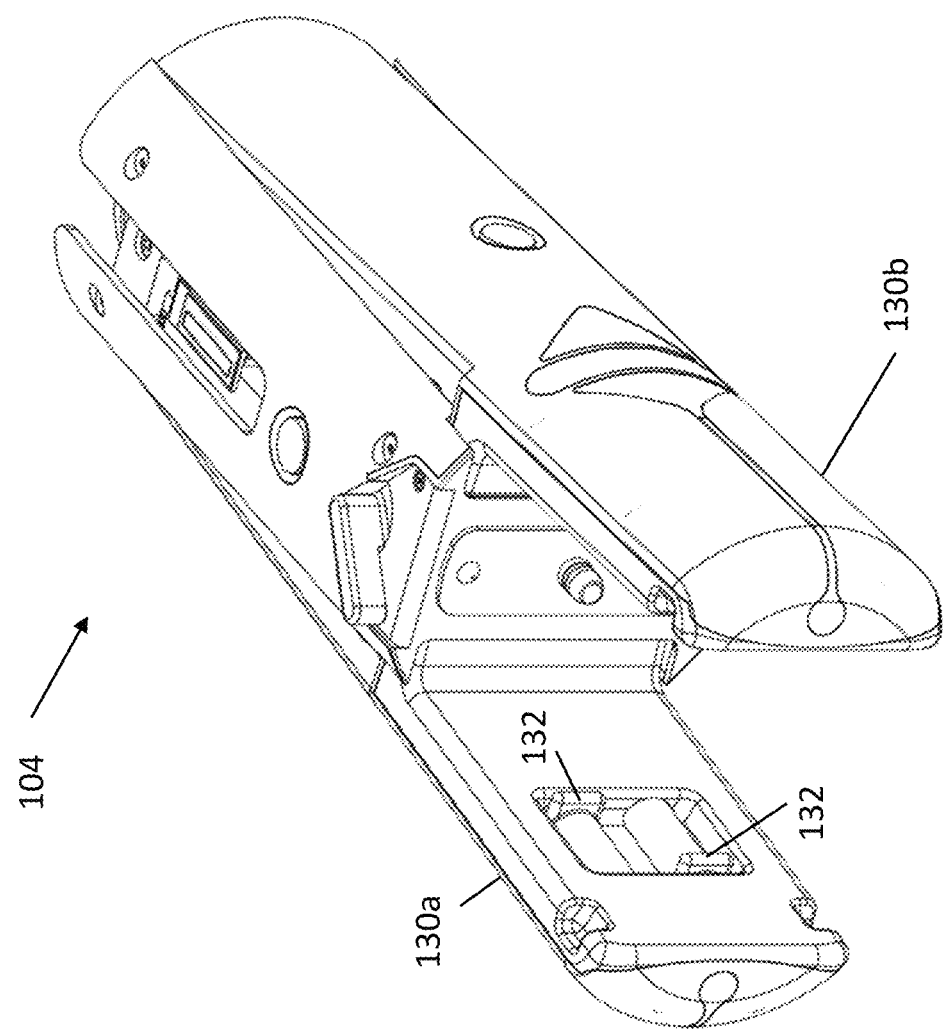
FIG. 8 shows the receiver of FIG. 2.
Figure 9:
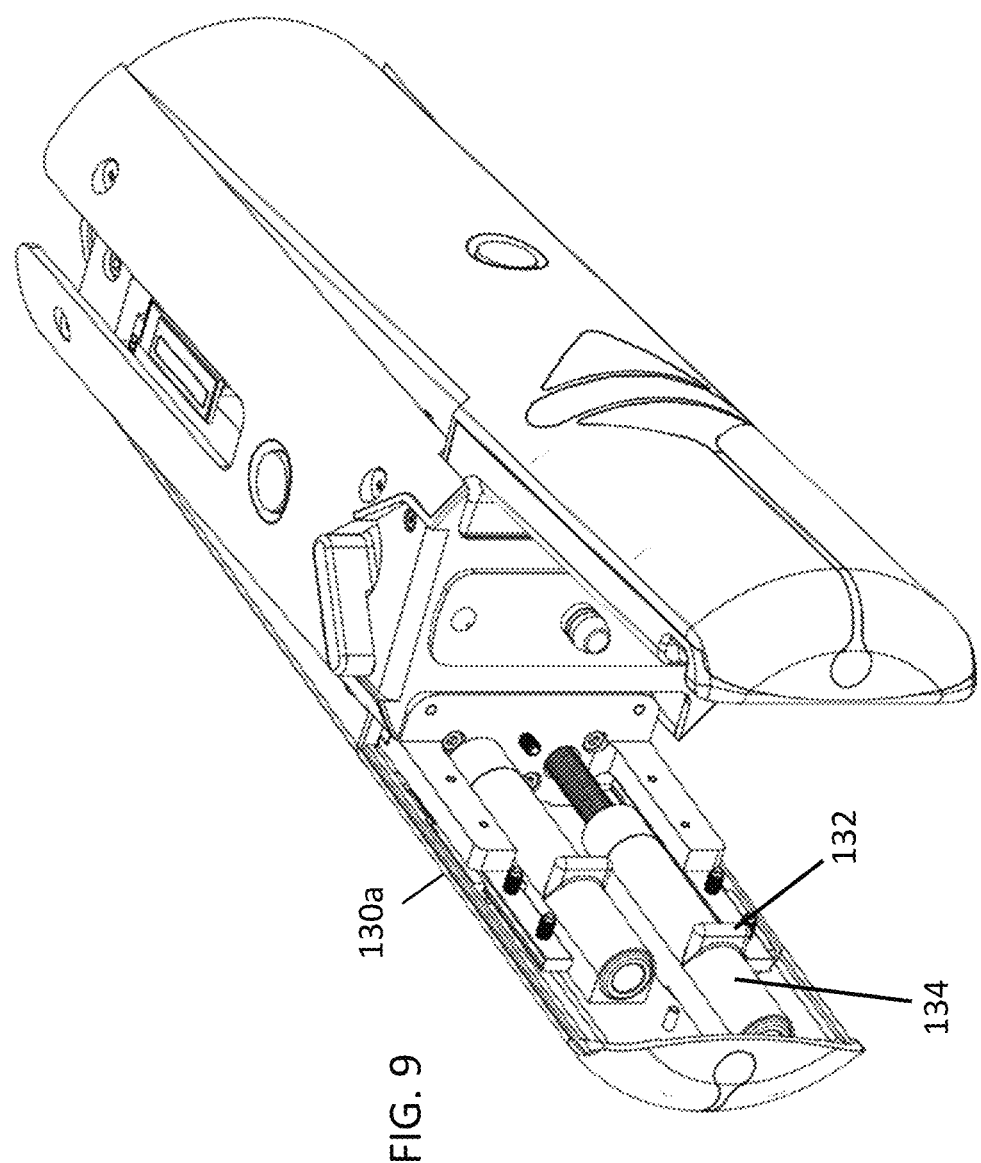
FIG. 9 is similar to FIG. 8 but shows a portion of the arm removed.

Referring to FIG. 8, the receiver 104 of the illustrated embodiment has a generally U-shaped cross section, having two elongate sides and a seat spanning between the two sides. The sides of the "U" are formed by a pair of distally-extending arm sections 130a, 130b, giving the receiver an opening into which the base 110 is received when the system is assembled (FIG. 3). Drive members 132, which will also be referred to as "drive outputs," extend inwardly from the arm sections 130a, b. They are positioned so that when the instrument is mounted to the receiver 104, each drive input member 122 of the instrument (FIGS. 5 and 6) is in contact with a corresponding one of the drive output members 132. Two drive members 132 are visible in FIG. 8. Two others extend from arm 130b but are obscured in the drawing. In FIG. 9, a portion of the arm 130a is removed to show that the drive members 132 are carried by carriages 134 housed within the arms 130a, 130b. Motors 136 within the receiver 104 (FIG. 10) drive linear movement of the carriages 134, and thus the drive members 132, along their respective arm sections 132a, b.

The type of contact between the drive members 132 of the receiver and their counterpart driven members 122 of the instrument is selected based on the nature of the drive motion that is transferred to the drive members 122. In the linear drive configuration shown, the components may be configured so that a carriage of the instrument can be pushed, pulled, or both pushed and pulled, by the corresponding drive component of the receiver. Additionally, different carriages may be configured differently, with some only pushed and others only pulled (or some other combination of push, pull, and bi-directional drive).

Where motion is driven in a single direction, contact between the drive members 132 and the driven members 122 is only needed in the direction of motion. In FIGS. 3-10, the drive members 132 and the driven members 122 are configured so that the drive members 132 push the driven members in the distal direction, but need not pull the driven members in the proximal direction due to the presence of the springs 124 discussed in connection with FIG. 7. Thus, the face or region of each drive member 132 facing the direction of motion (here the distal direction) contacts the driven member 122. Thus, in this example, it is not necessary that the drive members and driven members be mated to one other or otherwise engaged, although they could be. Instead, these members 122, 132 can be simply configured to have opposed surfaces (which may optionally be planar) that contact one other. If motion was driven in the proximal but not distal direction in this embodiment, the proximal face of the drive member would contact the driven member.

In other embodiments motion of a driven member is driven in two directions. In a linear drive arrangement such as is shown in the drawings, this might mean that the drive member can both pull and push the driven member. In such embodiments, the drive member and driven member are configured to be engaged, mated, or otherwise designed to be in contact regardless of the direction of motion. For example, FIG. 11 shows an alternative carriage 120a for the instrument, which includes a driven member 122a shaped to mate with the drive member 132 (FIG. 10).

FIG. 12 shows receiver carriages on which the drive members 132a are comprised of the walls of a female receptacle shaped to receive a driven member 122 of the type shown in FIG. 5. FIG. 13 shows receiver carriages having two different drive member designs. On the upper carriage the drive member 132 is similar to those previously discussed. On the lower carriage the drive member 132a is comprised of the walls of a female receptacle shaped to receive a driven member 122 of the type shown in FIG. 5. In this configuration, the upper carriage might drive the corresponding driven member in a single direction (push or pull), while the lower carriage might drive the corresponding driven member in both push and pull.

The receiver 104 may be one that expands to receive the base 110. In this embodiment, the receiver 104 is moveable from a closed position to an open position by increasing the separation between the arms 130a, 130b. Once moved to an open position, any instrument held by the receiver can be removed, and the base of a first or replacement instrument may be received. The receiver is also moveable to reduce the separation between the arms as it moves from the open position to a closed position in which the base is captured 110 by the receiver 104. When in the closed system with a base 110 between the arms 130a, b, the drive inputs 122 of the base are operatively engaged (albeit not necessarily physically engaged as discussed above) with the drive outputs 132 of the receiver.

Figure 14:
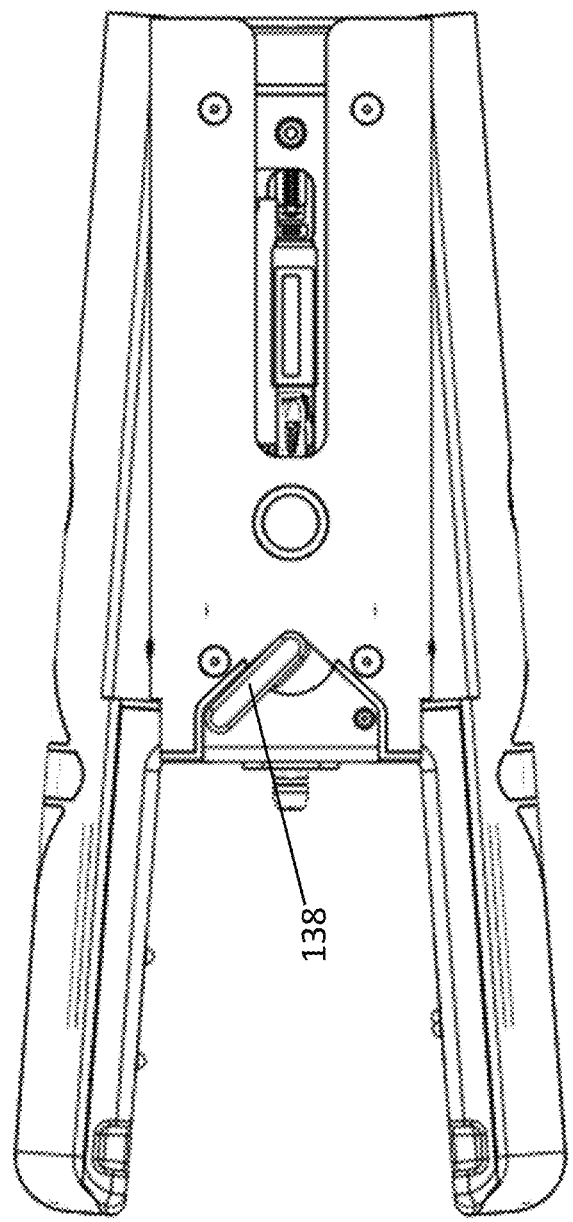
FIGS. 14 and 15 are top plan views of the receiver, showing it in the open and closed positions, respectively.
Figure 15:
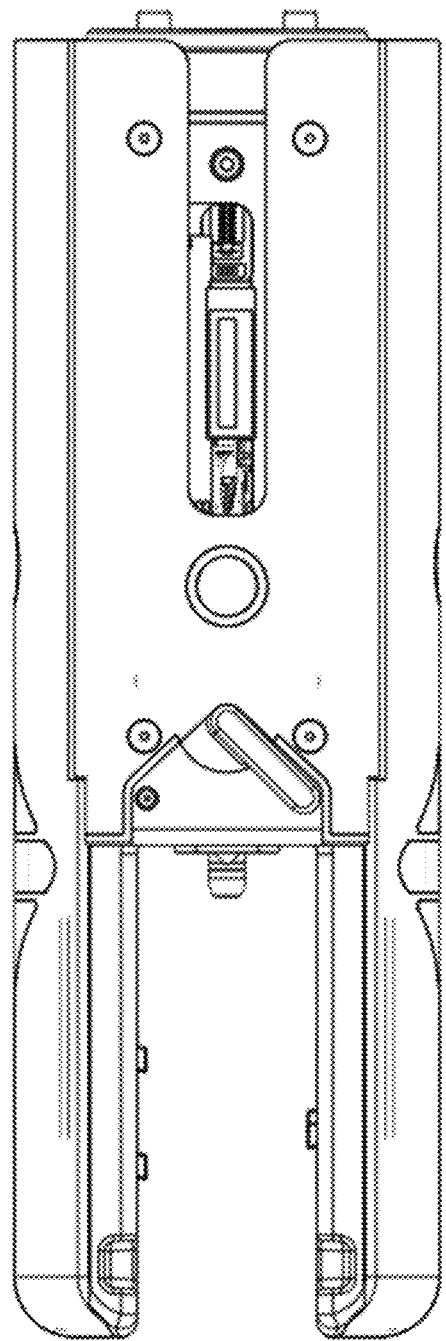

Expansion may be achieved in various ways. In the example shown in the drawings the arms 130a, 130b pivot between the opened position (FIG. 14) and the closed position (FIG. 15). In other configurations they may move in parallel. When the receiver is closed to engage the base of the instrument, the arms of the receiver 104 reach around both sides of the base 110 to retain the base and to position the drive outputs where they will move the drive inputs to actuate degrees of freedom or other functions of the instrument as described.

The receiver may be selectively opened and/or closed manually or electromechanically my moving the arms towards/away from another. In the first embodiment, the arms 130a, 130b are pivoted relative to their proximal ends by a rotatable lever or knob 138 having linkages 140 spiraling outwardly from it. When the lever/knob is manually rotated in a first direction, the linkages 140 cam the arms 130a, b to the open position. Rotating the lever/knob in the opposite direction cams the arms to the closed position. In addition, or as an alternative, the linkages 140 may be rotated by actuation of a motor 142. A switch 144 on the receiver 104 may be used by a surgical assistant to activate the motor 142 to readily open and then close the receiver during an instrument exchange.

Figure 22:
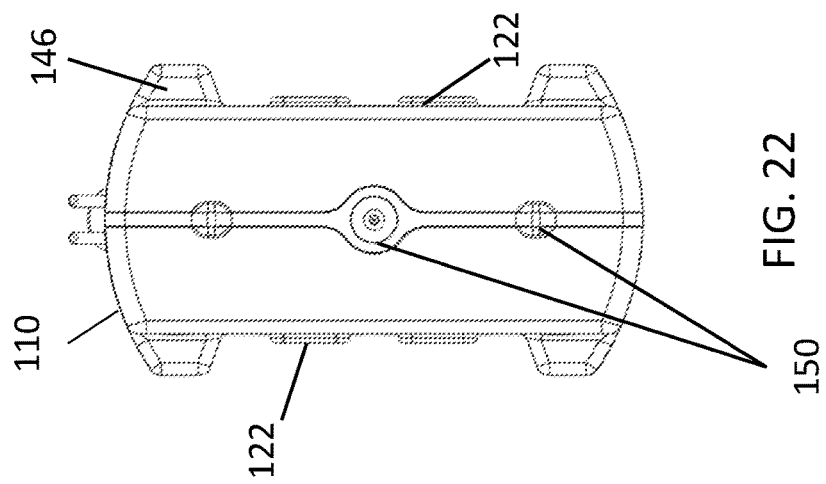
FIG. 22 is a rear plan view of the base of the instrument.
Figure 21:
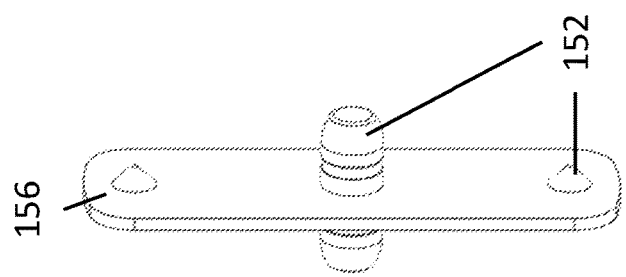
FIG. 21 is a perspective view of the drape connector.

The system may include features to facilitate alignment and retention of the instrument adapter while the actuator assembly of the manipulator arm is open. Examples include tabs 146 on the base 110 or receiver 104 that are received in corresponding seats 148 (FIG. 20) of the receiver 104 or base 110. The proximal face of the base 110 may additionally include alignment features. FIG. 22 shows female parts 150 (e.g. recesses, divots, holes or similar alignment features) that receive male parts 150 (FIG. 21) as discussed in connection with the drape, below. As such, this embodiment has engaging and/or controlling features on three sides of the base 110. It should be understood that control points (drive inputs) may exist on any side of the base and may be actuated by either the electromechanical actuators of the receiver/manipulator, or by operating personnel at the bedside. Additionally, these control points may share axes, have parallel axes, slide linearly along the same plane, or may be a combination of movements that are not related (i.e. not planar, parallel or sharing the same axis).

Lastly, it is not required that the base have defined planes or interface points. For example, an adapter body may be spherical or cylindrical in nature, where the control points are arranged across the surface(s) of the body.

A second embodiment is similar to the first, having a "U" construction, but instead of angling the two sides of the "U" to reach the open position, the sides expand while keeping the internal surfaces parallel. In this embodiment, a four-bar mechanism can be used, in concert with a lever or knob system or motor to drive the opening and closing of the system.

Each of these concepts allows expansion of the space between the "U" sides, and this feature enables the acceptance of varying widths of bases for instruments, cameras, or other adapters (e.g. a removable adapter on the proximal end of the camera or instrument, allowing cameras or instruments from various manufactures to be used with the system). For instruments having bases of different widths, the system would identify the instrument and close down the appropriate amount to hold the instrument base or adapter rigidly. For example, a non-contact reed switch board could be used to identify instruments or adapters of varying widths. One digital reading would result in a closure to a 30 mm space between the arms 130a, b, while another may result in 40 mm. For a mechanical solution, a lever system could be used where the instruments push with varying distances on the lever system. For example, a lever system may allow inputs from 0-4 mm, where 0 mm is fully open and 4 mm is fully closed. One instrument may push 4 mm to result in a 30 mm space between the arms 130a, b, or full closure, while another may push 3 mm to result in a 40 mm space.

It should be noted that the shape and size of the "U" and in the space defined by the arms 130a, b can be adjusted to accommodate a wide variety of instruments or adapters. Additionally, while the "U" shape may be preferable for this application, other shapes having at least two partially opposing sides may be used, where the sides may not have parallel, opposing faces.

A further advantage of the "U" shaped embodiments is the ability to engage some instruments such that the instrument shares the axis of the receiver, but to engage others such that the instrument does not share the axis. For example, the receiver engaged with a camera system may be able to hold the camera so that the camera shaft and the receiver axes are at an angle, up to 90 degrees, relative to each other. This would allow the camera and light cords to pass "though" the receiver, rather than having to pass around it. Other instruments, such as harmonic energy devices or staplers may benefit from this feature as well, while allowing the mass of the instrument to be as close to the 6DOF force sensor as possible.

Figure 20A:
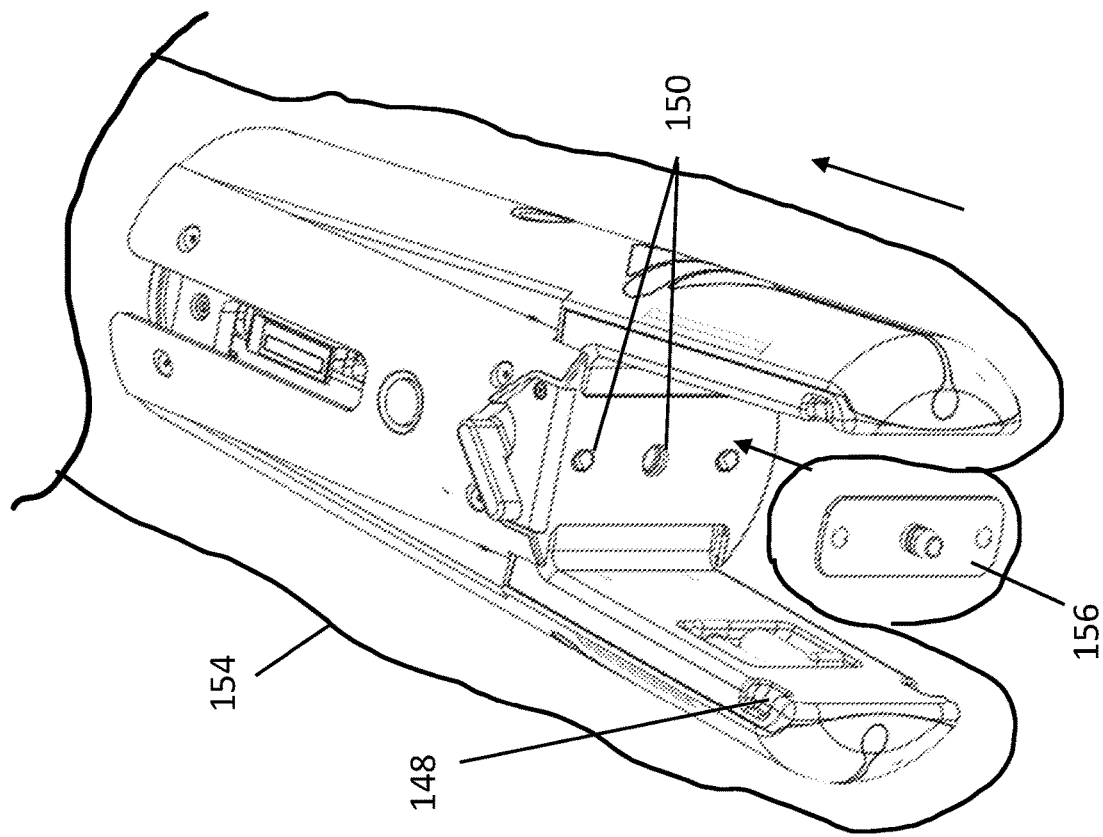
FIG. 20A is a perspective view showing the receiver as it is being draped.
Figure 20B:
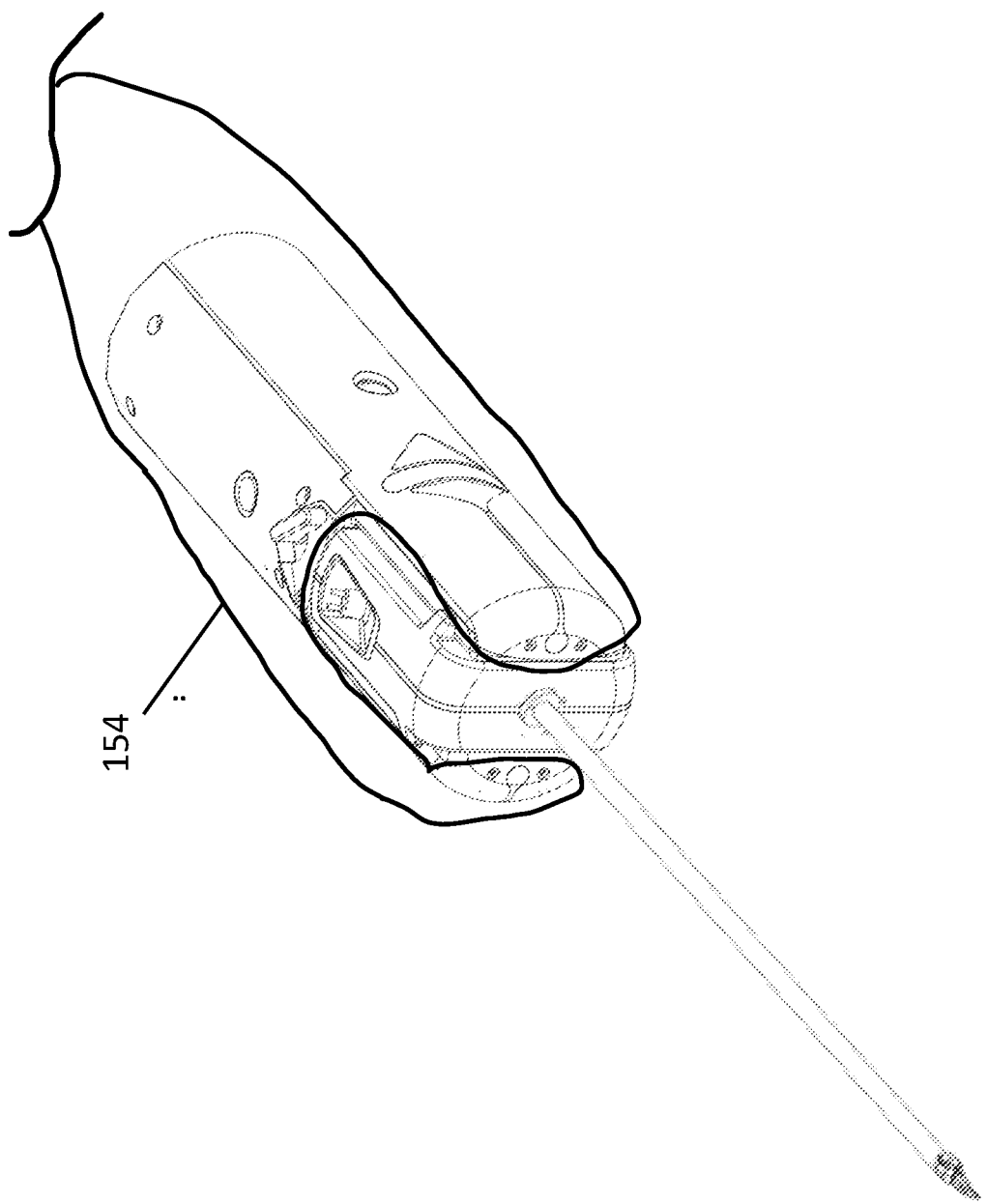
FIG. 20B is similar to FIG. 16 but shows the drape in place.

Referring to FIGS. 20A and 20B, the receiver 104 is typically a non-sterile component that is covered by a sterile drape 154 or barrier before attachment of the sterile surgical instrument. At the interface between the drive elements and the driven elements, the motion described above is communicated through the drape to control the degrees of freedom of the instrument. In one embodiment of a drape 154, the drape material is shaped to fit with the geometry of the receiver, having two "fingers" to cover the arms 130a, b that open and close. It is optimal to ensure that the drape is properly oriented with the receiver and that the area for the instrument is clear for instruments to be engaged and removed. In this embodiment, the drape includes an embedded plastic "drape connector" 156 adhered such that the connector has geometry extending to both sides of the drape. One side of the drape connector includes mating pins, posts, conical elements etc. that mate with female parts (e.g. recesses, conical divots, holes or similar alignment features) in the seat of the receiver 104, while the other mates with the female parts 150 on the proximal face of the base. The mating pins may provide retention force to both the manipulator and instrument as well as the orientation of the drape and instrument.

In this embodiment, the central male element 152 of the drape connector has two annular rings that allow mating geometry to snap into, providing the retention force. In this case, the mating geometry may be a coiled spring. During the draping process, the drape is positioned over the arms 130a, b of the receiver. The inward-facing face of the drape connector 156 is positioned so that the male members are inserted into the female parts at the seat of the receiver, and the outward-facing face of the drape connector is similarly snapped into engagement with the proximal face of the instrument base 110.

Because the drape connector extends through both sides of the drape, it may be used as a sterile conduit for a variety of mechanical, electrical, optical or other tasks. A non-inclusive list of these features or tasks is included below.

The drape connector may be used to provide electrical signals including power, ground, communication, etc. between the robotic manipulator and the instrument This electrical energy may be used to power instrument recognition devices such as RFID transceivers, cameras, proximity sensors or switches (including hall sensors and reed switches). These devices may be able to determine what instrument shaft is attached to a given base/adapter, while allowing certain bases/adapters to be common for a variety of instrument types.

This energy could also power sensors such as force and torque or displacement devices as a means of measuring activity within the instrument or the instrument adapter. These measurements may enable better instrument control or user feedback such as force feedback or tactile responses.

This electrical energy could be used for monopolar/bipolar or advanced energy devices, eliminating the need for cables that can get wrapped around the manipulator or instrument when the manipulator is rotated.

The drape connector may be used to provide optical signals or light transmission between the robotic manipulator and instrument These optical signals may be used for communication purposes including instrument identification via spectroscopy or other methods These optical signals could be mated with a rod lens scope to gain an intraoperative viewpoint without requiring a camera head as with other endoscopes The optical signals could be coupled with sensors such as fiber optics for measuring deflection, for example. This deflection could be used to interpret force on an instrument or adapter.

The drape connector may be used for other features as well. In this embodiment, for example, the proximal surface of base has a flush port that is intended to be used to clean the instrument adapter and instrument shaft after a surgical procedure. If left open during the procedure, this flush port is a leak pathway for $CO_2$ to exhaust from the operative site. The drape connector is used to plug this flush port, eliminating the leak pathway, while also eliminating components in the instrument adapter such as check valves or elastomeric flush port covers.

Second Embodiment

As discussed, in the first embodiment, the assembly is configured to transfer linear motion of a push/pull variety from the drive outputs to the drive inputs, but other embodiments can be envisioned in which rotary, or a combination of linear and rotary motion, can be transferred. See, for example the second embodiment of FIGS. 23-25, which show an alternate base 110b. Here each of the drive elements 122b extends from a pulley 123 rotatably mounted to a structure (e.g. partition) within the base. Each cable is coupled to a corresponding one of the pulleys 123. The linear motion of the drive outputs 132 (FIG. 8) causes rotation of the corresponding pulleys 123 and thus alteration of the tension in the cables. This effects movement or actuation of the end effector as described in connection with the first embodiment. An expansion spring 125 may serve to return the pulley to the unbiased position when the drive member removes or reduces the force against the driven member, in a manner similar to that described with the first embodiment.

Drape Incorporating EMI Shielding

Figure 26A:
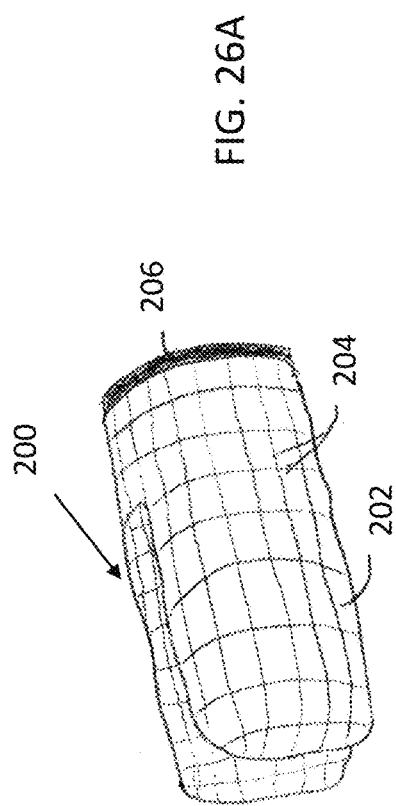
FIG. 26A shows an example of a drape having integral EMI shielding.
Figure 26B:
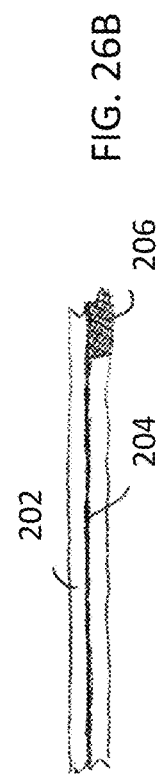
FIG. 26B is a cross-section of a portion of the drape shown in FIG. 26A.
Figure 26C:
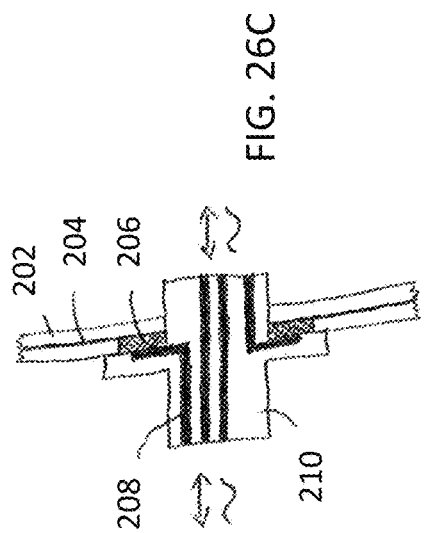
FIG. 26C is similar to FIG. 26B, but shows an embodiment including electrical connectors and terminations incorporated into the drape

The manipulator and related components may be covered by drapes using a variety of material types suitable for surgical draping. One example of a drape that may be used will next be described in connection with FIGS. 26A-26C. It should noted that this drape may be used to drape the disclosed components, to drape components of alternative surgical robotics systems other than those described above, and to drape many other components of sterile equipment (other than surgical robotic systems).

If used with the embodiments described here, the drape might be positioned as shown in FIGS. 20A and 20B, over the receiver 104 of that embodiment before insertion of the proximal body 110 into the actuator assembly.

The drape 200 is formed of a stretchable, multi-ply polymer containing integral circuits printed with electrically conductive (or insulating) inks 204. The printed circuits may serve as a flexible Faraday cage to shield the contained device from electrostatic discharge and/or electromagnetic interference. The ink may be printed in a mesh pattern or other pattern suitable to create Faraday shielding. The printed circuits may also serve as passive functional circuits such as capacitive sensing (buttons), resistance sensing (strain measurement), antennas (RFID), etc. The printed traces may be sandwiched between laminations 202 of drape material. Where electrical signals are to be transferred from one side of the drape to the other, the printed traces may be connected to conductive pads 205 for transferring electrical signals into and out of the printed circuits. Likewise, the printed circuits may connect to molded in components and features such as connectors 210 and vias 208. The drape may take any form that is desired and may be formed from a flat sheet (or roll) of material.

Drape 200 provides a low cost and efficient means of shielding an instrument driver from ESD or EMI generated by high energy instruments that may be mounted to it. In shielding applications, this method reduces the complexity of designing electrical seals (such as springs) between moving interfaces in the device and eliminates the need to add electrically conductive plating to external covers. It may also be used to span gaps in the enclosed device which may otherwise be difficult to shield. It also can add functionality to the distal drape on a surgical robotic arm.

Graphical User Interface on Manipulator

A graphical user interface may be positioned on the manipulator. This feature may be applied to any surgical robotic manipulator and while it is suitable for use with the configurations described above, it is equally suitable for use on components of other surgical robotics systems.

In some robotic systems, for the convenience of surgical personnel, each manipulator may be individually identified using color coding, color coded tape, numbers, or other markings in one or more locations on each manipulator. Additionally, the cart supporting each manipulator may include a screen for displaying error messages, and a series of lights to indicate machine status.

At times during the course of a surgical procedure, it may become necessary for a surgical assistant or other operating room employee to reposition the manipulator. This may be done by applying a manual force to the robotic arm and physically moving the robotic arm to the desired orientation or position. This may be a purely manual activity as with the prior art system, or it may be a power assisted activity. In either case, it would be advantages to notify the user about forces on the instrument when the user is performing a manually driven motion. Typically, to move the manipulator when it is not being actively teleoperated from the surgeon console, the user takes an action (e.g. simultaneously depresses two buttons on the manipulator) to unlock the manipulator so s/he can manually move the end effector of the manipulator to a desired position.

This section describes embodiments that consolidate functions of instrument status and error messages communication, manipulator identification and an easily accessible touch point for manipulation of the arm by a user, at a single site on the manipulator arm that is easily accessible by the user regardless of the manipulator's end effector orientation.

A first embodiment includes a surgical robotic system comprising at least one manipulator arm. As shown in FIG. 27, the manipulator arm (e.g. 13, 14, 15 of FIG. 1) has an end effector distal to at least one degree of freedom of the manipulator arm. In this specific embodiment, the receiver 104 is part of the end effector. In use, as described above, a surgical instrument 106 is removably attachable to the end effector.

On the end effector is a capacitive display screen 212 on which a variety of information can be displayed. In this embodiment, the display screen 212 is cylindrical, and extends around the body of the end effector. The screen may be configured to change colors, display text or icons or other GUI items in order to communicate machine status, arm identification, instrument identification, etc to the user. Icons could be displayed and selected via touching the capacitive screen to perform tasks such as calibration, homing or docking the end effector to the trocar.

Additionally, touch gestures by the user on the capacitive screen could elicit a response by the machine. For example, touching in two points spaced apart could unlock the degrees of freedom to allow manipulation or manual movement of the manipulator about its joints. Swiping could change between menus or tell the machine to go to a specific state (draping, etc). Gesture interaction with the display could also be used to cause the system to place the manipulator in a state for, and/or cause activation of the manipulator's actuators to configure the manipulator in a position or orientation suitable for executing different tasks (docking an instrument, exchanging instruments, calibration, homing, storage, draping, etc)

In a preferred configuration the touch screen wraps entirely around the end effector. In this configuration, the capacitive points can always be accessed easily. Additionally, the inclusion of an inertial measurement unit (IMU) on or in the end effector provides feedback to the system indicating the orientation of the end effector. Based on this feedback, the system would maintain or alter the position and orientation of messages and menus displayed on the GUI so that from the viewpoint of an operator the messaging/menus are always in a specific orientation, regardless of the rotation of the end effector relative to the operator. In order words, the IMU would detect the orientation of the end effector, and a processor of the system would select a region of the screen that would be visible to a user in that orientation, and cause the relevant messaging and menus to be displayed in that region and, preferably, in an easily readable orientation for the user.

This feature enhances convenience of the surgical system use by including all of the available information about the system on display at a location that is easily accessible at the patient-side. Touch points may be wrapped around the entire end effector, meaning they are always accessible and in the same location (from the user's perspective), regardless of the end effector's orientation. The display may include color changing displays that allow the use of color to indicate different operative states, or identification of different arms to the users.

Force Notification During Manually Driven Motion of a Manipulator

As discussed in the above section, at times during the course of a surgical procedure, it may become necessary for a surgical assistant or other operating room employee to reposition the manipulator. This may be done by applying a manual force to the manipulator and physically moving the manipulator to the desired orientation or position. This may be a purely manual activity as with some commercially available systems, or it may be a power assisted activity. In either case, it would be advantageous to notify the user about forces on the instrument when the user is performing a manually driven motion.

As also discussed in this application, a force/torque sensor, which may be a 6DOF force/torque sensor, may be attached to the manipulator and used for determining the haptic information needed to provide force feedback to the surgeon at the user interface. FIG. 28 an end effector as described above. Within the manipulator, in a region proximal to the instrument position, is a 6DOF force/torque sensor 214 which, as discussed above, is used to measure forces experienced by the surgical instrument so that the system can communicate those forces to a user via a haptic interface. Proximal to the sensor 214 is at least one notification component 216, which may be at least one of a vibrational transducer, and a visual indicator or light emitter. Where a vibrational transducer is used, positioning it on the manipulator in a position proximal to the sensor 214 helps avoid interference with force measurements of the sensor 214. The visual indicator may be a light, LED or collection of LEDs, image display, etc. If a GUI of the type described in the previous section is used, it may be part of that GUI. These components are used to alert the user to the presence of forces against the instrument while the system is being manually repositioned.

During a manual driven motion (motion performed by the user controlling the movement of the arm with his/her hand on the arm), when a force is applied on the instrument attached on the arm, a vibration and a visual alert from the light emitter are emitted. This alerts the person moving the arm that the instrument is contacting tissue or another structure, so that additional precautions can be taken if warranted. This would be particularly beneficial if, for example, an instrument is being inserted into a trocar positioned at the incision site while the instrument is engaged to the arm.

The visual indicator may be configured to provide directional information to the user to advise the surgeon. For example, it may provide a visual indication of the direction the arm should be moved in order to alleviate the forces between the instrument and the tissue or other object. If the light emitter is a ring of lights or LEDs encircling a portion of the arm, a quadrant of those lights might be illuminated to mark the direction the user should push the arm in, or the direction of the force against the instrument. If a flexible display or GUI is used, one or more arrows or other symbols, icons, text etc. may be displayed for the same purpose. In some embodiments, the system may be configured to cause the amplitude/frequency of the vibration and the intensity/blinking of the light to be proportional to the measured force on the force sensor 214.

During a remote driven motion (motion performed by the user controlling the arm remotely using one of the user input devices 17, 18), when a force is applied to the instrument attached on the arm (or if a force exceeding a defined threshold is applied), a visual alert from the light emitter may be emitted.

This feature may be used for any robotic manipulator and is not limited to the embodiments described here. In general, it will be part of a surgical robotic system comprising a manipulator arm including a force and torque sensor, a surgical instrument mountable to the manipulator arm, a haptic user input device. The system includes at least one processor, and at least one memory storing instructions executable by said at least one processor to do the following: in response to user manipulation of the haptic user input device, cause the manipulator arm to move the surgical instrument, in response to signals from the sensor during user manipulation of the haptic user interface, causing actuators of the haptic user input device to apply force feedback to the haptic user input device, and in response to signals from the sensor during manual user movement of the manipulator arm, activate a vibration transducer on the arm. The instructions may be further executable by the at least one processor to, in response to signals from the sensor, activate a visual alert on the arm.

Note that the vibrational transducer may be used to provide other types of feedback to the user in addition to or as an alternative to force feedback. For example, if the system is configured to use the force/torque to determine the fulcrum point for instruments passing through the incision as described in U.S. Pat. No. 9,855,662, the vibrational alert may be activated to notify the user that the fulcrum determination process is complete and the fulcrum has been set.

While certain embodiments have been described above, it should be understood that these embodiments are presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Moreover, features of the various disclosed embodiments may be combined in various ways to produce various additional embodiments.

Any and all patents, patent applications and printed publications referred to above, including for purposes of priority, are incorporated herein by reference.

We claim:

1. A robotic manipulator having an actuator assembly at its distal end, the actuator assembly including:

a first arm and a second arm having opposed first and second faces defining an instrument-receiving portion between the first arm and the second arm, at least one of the first arm and second arm moveable relative to the other of the first and second arms to move the actuator assembly between a first position in which the first and second arms are spaced by a first distance, and a second position in which the first and second members are spaced by a second, larger, distance;
a first carriage carried by the first arm, the first carriage having a first drive element extending into the instrument-receiving portion;
a first motor in the actuator assembly operable to move the first carriage relative to the first arm;
a second carriage carried by the second arm, the second carriage having a second drive element extending into the instrument-receiving portion;
a second motor in the actuator assembly operable to move the second carriage relative to the second arm.

2. The manipulator of claim 1 wherein, the first carriage is positioned within the first arm, with the first drive element extending from within the first arm to the instrument-receiving portion, and wherein the second carriage is positioned within the second arm and with the second drive element extending from within the first arm to the instrument-receiving portion.

3. The manipulator of claim 1, wherein the first and second faces are parallel to one another when the first arm and the second arm are in the first position.

4. The manipulator of claim 1, further including a third motor operable to move said at least one of the first arm and the second arm to move the actuator assembly between the first position and the second position.

5. The manipulator of claim 1 where the robotic manipulator includes a pass-through for instrument or camera cables.

6. The manipulator of claim 5, wherein the pass-through extends through a portion of the actuator assembly.

7. The manipulator of claim 1, wherein the first carriage includes a first drive element extending into the instrument-receiving portion and the second carriage includes a second drive element extending into the instrument-receiving portion, each of the first drive element and the second drive element translatable relative to the manipulator by its corresponding carriage.

8. The robotic manipulator of claim 7, wherein at least one of the first drive element and the second drive element is translatable in a longitudinal direction relative to a longitudinal axis of the surgical instrument.

9. The robotic manipulator of claim 8, wherein each of the first drive element and the second drive element is translatable in a longitudinal direction relative to a longitudinal axis of the surgical instrument.

10. The robotic manipulator of claim 1, wherein in the second position the instrument-receiving portion is configured to be expanded to permit passage of a base of a surgical instrument between the first face and the second face, and wherein in the second position the instrument-receiving portion is configured to be partially closed to engage the base of the surgical instrument between the first arm and the second arm.

11. The robotic manipulator of claim 1, wherein in the second position the instrument-receiving portion is configured to be expanded to permit passage of a base of a surgical instrument between the first face and the second face, and wherein in the second position the first carriage and the second carriage are positioned to permit operative engagement of the drive elements and corresponding drive inputs of the base during operation of the first motor and the second motor.

12. The robotic manipulator of claim 1, wherein at least one of the first arm and the second arm is pivotable from the first position to the second position.

13. The robotic manipulator of claim 1 wherein at least one of the first arm and the second arm is translatable from the first position to the second position.

14. The robotic manipulator of claim 1 wherein at least one of the first arm and the second arm is slidably translatable from the first position to the second position.

15. A robotic system assembly comprising:
an actuator assembly, the actuator assembly including a first arm and a second arm having opposed first and second faces defining an instrument-receiving portion between the first arm and the second arm, the actuator assembly further including;
a first drive element extending from the first arm into the instrument-receiving portion and a first motor operable to advance the first drive element relative to the actuator assembly;
a second drive element extending from the second arm into the instrument-receiving portion and a second motor operable to advance the second drive element relative to the actuator assembly, wherein the first and second motors are independently operable to independently advance the first and second drive elements;
a surgical instrument having a body removably positionable within the instrument-receiving portion of the actuator assembly, the body including a first control input and a second control input, each control input moveable relative to the body to actuate movement of at least a portion of the surgical instrument wherein the first and second control inputs are operatively associated with corresponding ones of the first and second drive elements when the bod is engaged in the instrument-receiving portion of the actuator assembly.

16. The robotic system assembly of claim 15 wherein the first and second control inputs extend from the body in opposite directions.

17. The robotic system assembly of claim 15 wherein the first and second control inputs extend from the body in non-parallel directions.

18. The robotic system assembly of claim 15, wherein the first and second control inputs extend from the body in parallel directions.

19. The robotic system assembly of claim 18, wherein a sterile barrier is disposed between the drive elements and the control inputs when the surgical instrument is mounted to the robotic manipulator.

20. The robotic system assembly of claim 15, wherein the actuator assembly is moveable between an open position in which the actuator assembly is configured to receive the body to a closed position in which the first and second control inputs are operably associated with first and second drive elements of the actuator assembly.

* * * * *